(12) United States Patent
Nielsen et al.

(10) Patent No.: US 6,312,415 B1
(45) Date of Patent: Nov. 6, 2001

(54) OSTOMY APPLIANCE

(75) Inventors: Inger Mann Nielsen, Frederiksberg; Eskil Hoejland Olsen, Klampenborg; Laila Busk Gothjaelpsen, Hvidovre, all of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/424,229

(22) PCT Filed: May 25, 1998

(86) PCT No.: PCT/DK98/00211

§ 371 Date: Feb. 29, 2000

§ 102(e) Date: Feb. 29, 2000

(87) PCT Pub. No.: WO98/53772

PCT Pub. Date: Dec. 3, 1998

(30) Foreign Application Priority Data

May 26, 1997 (DK) ................................................ 0597/97

(51) Int. Cl.[7] .................................................... A61F 5/448
(52) U.S. Cl. .......................... 604/342; 604/327; 604/332; 604/336; 604/337; 604/338; 604/339; 604/341; 604/343; 604/344
(58) Field of Search .................................... 604/327, 332, 604/336–339, 341, 342, 343, 344

(56) References Cited

U.S. PATENT DOCUMENTS

| 3,876,771 | | 4/1975 | Denner ..................................... 424/78 |
| 4,204,540 | | 5/1980 | Cilento et al. ......................... 128/283 |
| 4,367,732 | | 1/1983 | Poulsen et al. ....................... 128/156 |
| 4,551,490 | | 11/1985 | Doyle et al. ............................ 524/22 |
| 4,750,482 | | 6/1988 | Sieverding ............................ 128/156 |
| 4,850,985 | * | 7/1989 | Edwards et al. ..................... 604/339 |
| 5,125,917 | * | 6/1992 | Whealin ................................ 604/340 |
| 5,369,130 | | 11/1994 | Numata ............................... 514/772.3 |
| 5,380,309 | * | 1/1995 | Keyes et al. ......................... 604/308 |
| 5,429,625 | * | 7/1995 | Holmberg ............................. 604/338 |
| 5,520,670 | * | 5/1996 | Blum .................................... 604/338 |
| 5,618,276 | * | 4/1997 | Leise, Jr. et al. .................... 604/336 |
| 5,626,079 | * | 5/1997 | Battles et al. .......................... 442/60 |
| 5,722,965 | * | 3/1998 | Kuczynski ............................ 604/344 |
| 5,865,820 | * | 2/1999 | Myello et al. ........................ 604/345 |
| 5,935,115 | * | 8/1999 | Espina .................................. 604/277 |
| 6,210,384 | * | 4/2001 | Cline .................................... 604/338 |

FOREIGN PATENT DOCUMENTS

| 0 048 556 | 3/1982 | (EP) . |
| 0 686 381 | 12/1995 | (EP) . |
| 2 041 753 | 9/1980 | (GB) . |
| 1 587 604 | 4/1981 | (GB) . |
| 2 244 651 | 12/1991 | (GB) . |
| 2 290 974 | 1/1996 | (GB) . |
| WO92/18074 | 10/1992 | (WO) . |

OTHER PUBLICATIONS

Hellman, J. et al, "Dermatologic Complications in Colostomy and Ileostomy Patients", International Journal of Dermatology, 29(2), 1990, pp. 129–133.

Pearl, R. et al, "Early Local Complications from Intestinal Stomas", Arch. Surg., vol. 120, Oct. 1985, pp. 1145–1147.

* cited by examiner

*Primary Examiner*—John G. Weiss
*Assistant Examiner*—Michael Bogart
(74) *Attorney, Agent, or Firm*—Jacobson Holman, PLLC

(57) ABSTRACT

The invention relates to an ostomy appliance comprising a body side member comprising an adhesive wafer or pad for securing the appliance to the user's skin, the wafer or pad having a hole for receiving a stoma, and a separately exchangeable receiving member or bag secured to the body side ostomy member for receiving secretions from the ostomy, the ostomy appliance further comprising a separate sealing member disposed in the hole of the wafer or pad surrounding the stoma wherein the separately exchangeable receiving member or bag is secured releasably to the body side ostomy member by a mechanical fastening means.

6 Claims, 2 Drawing Sheets

OSTOMY APPLIANCE

FIELD OF THE INVENTION

The present invention relates to an ostomy appliance, and the use of a mechanical fastening means for securing a separately exchangeable receiving member or bag for receiving secretions from an ostomy to a body side ostomy member.

BACKGROUND OF THE INVENTION

In connection with surgery for a number of diseases in the gastro-intestinal tract a consequence is, in many cases, that the patient is left with an abdominal stoma such as a colostomy, an ileostomy or an urostomy. In such cases or in connection with a fistula the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving secretions from the ostomy in case of a two-piece appliance.

When using one-piece appliances, the whole appliance, including the adhesive wafer or pad securing the appliance to the skin is removed and replaced by a fresh appliance. When using two-piece appliances, the body side ostomy member is let in place for several days, and only the receiving member or bag is replaced.

The service time of the body side ostomy member depends on the amount and aggressiveness of the secretions and of the tightness between the ostomy and the body side ostomy member.

In the known appliances it is necessary to change the body side member of two-piece appliance when the centre part of the adhesive wafer or pad has been sufficiently deteriorated to allow access of the aggressive secretions to the skin surrounding the stoma, irrespective of the fact that the wafer as such has a much longer wearing time. The access of aggressive secretions to the skin is causing skin problems.

Skin problems are common for persons having a stoma. Generally, about 40% have skin problems (Pearl et. al. 1985 "Early local complications from intestinal stomas", Arch. Surg. 120; 1145–1147.) and the frequency is especially high for persons having an urostomy or ileostomy. About 80% of the persons having an ileostomy have skin problems (Hellman, J. D., Lago, C. P. 1990 "Dermatologic complications in colostomy and ileostomy patients", International Journal of Dermatology, 29 (2); 129–133.). The skin problems are mostly pronounced in a circular area about the stoma ½ inch from the stoma) (Hellman and Lago 1990).

Frequent changing of the body side member of a two-piece appliance or the frequent exchange of a one-piece appliance is undesirable due to the irritation of the skin and the quality of life may be improved and the nuisance of the wearing of an ostomy appliance reduced if the intervals between exchanging of body side member can be increased.

It is known to place a ring on the skin before applying the body side member or to make a filling between the edge of the stoma and the shaped whole of the ostomy appliance in order to form a seal between the stoma and the ostomy appliance in order to alleviate the problems using a commercially available medical grade adhesive paste. Such pastes are e.g. sold by Bristol-Myers Squibb under the trademark Stomahesive® or by Coloplast under the trade mark Coloplast® Paste.

These pastas, however, do not have a composition which has a sufficiently cohesion ensuring safe removal thereof without leaving residues on the skin and, on the other hand, the pastes often are so sticky that they cannot easily be shaped using the finger without sticking to the finger.

A paste should have a composition which is sufficiently tacky to secure the appliance or skin barrier to the abdomen, and cohesion ensuring safe removal thereof without leaving residues on the skin. On the other hand, the paste must not be so sticky that it cannot easily be shaped by a finger or hand without sticking to the hand. Furthermore, the paste must show a sufficient elasticity in order to be able to follow the movements of the patient without slipping the skin and should also show a great resistance to erosion caused by aggressive secretions from an ostomy.

In GB Patent Application No. GB 2 290 974 is disclosed an ostomy appliance wherein a body-side is combined with a mouldable mass of non-hypoallergenic, non-memory putty-like adhesive, particularly based on hydrocolloid or hydrogel.

GB Patent Application No. GB 2 290 974 discloses a body-side ostomy member comprising a ring to which a bag-side coupling ring or a bag can be attached, said ring comprising a rib and a flange, said flange being mounted on a wafer of medical grade adhesive having a central whole of diameter at least 65% of the internal diameter of the ring. A mouldable mass of non-hypoallergenic, non-memory putty-like adhesive, particularly based on hydrocolloid or hydrogel, is disposed radially inward of the wafer so that it forms a protective mass surrounding the stoma. The mouldable mass has a thickness of 1.25–3 times that of the wafer and a central hole therein of a diameter no more than 1/10 th of the internal diameter of the ring. Both the medical grade adhesive and the mouldable adhesive are adhered to the skin.

European Patent application No. EP 0 686 281 discloses an ostomy appliance comprising a collection pouch and faceplate assembly including a flexible patch having a stoma-receiving opening, a first layer of skinfriendly hydrocolloid-containing adhesive material along one side of said patch about said opening for securing said faceplate assembly to peristomal skin surfaces, and a second layer of relatively soft, easy-deformable and extrudable, adhesive sealant material of a composition that is resistant to being dissolved or disintegrated by stomal fluids and that immediately surrounds said opening; said second layer being displaceable inwardly and axially into said opening for forming a stoma-engaging annular gasket to prevent stomal fluids from contacting the peristomal skin and said first adhesive layer.

The mouldable mass of non-hypoallergenic, non-memory putty-like adhesive or flexible patch disclosed in GB Patent Application No. GB 2 290 974 and European Patent application No. EP 0 686 28 both are secured to the rim of the hole for receiving the stoma.

Published GB patent application No. 2 041 753 discloses an ostomy appliance comprising a body side member comprising an adhesive wafer for securing the appliance to the user's skin, said wafer having a hole for receiving a stoma, a stoma sealing duct and a separately exchangeable receiving member or bag secured to the body side ostomy member for receiving secretions from the ostomy, wherein the separately exchangeable receiving member is secured releasably to the body side member by a mechanical fastening means.

The ostomy appliances disclosed in GB Patent Application No. GB 2 290 974 and European Patent application No. EP 0 686 281 as well as GB patent application No. 2 041 753 suffer from the drawback that the mouldable sealing material is only foreseen to be changed together with the body side member of the appliance. There is no teaching nor indication that the mouldable sealing material might be exchanged separately without removing the body-side member from the skin. Such separate exchange is not possible either for the embodiments shown in the drawings of these applications.

It has suprisingly been found that it is possible to provide an ostomy appliance having a separate sealing member disposed in the hole of the wafer or pad surrounding the stoma offering a convenient and comfortable solution to the above problems and at the same time separating the two functions of the sealing around an ostomy and the securing of a separately exchangeable receiving member or bag for receiving secretions from an ostomy to a body side ostomy member.

None of the above mentioned patents describes the use of a separate sealing member which may be exchanged or substituted separately.

This idea according to the invention differs from the above mentioned patents since the central ring in this case can be substituted without substituting the adhesive of a body side member which carries the bag and in that the securing of a separately exchangeable receiving member or bag for receiving secretions from an ostomy to the body side ostomy member is separated from the sealing around the ostomy.

BRIEF DESCRIPTION OF THE INVENTION

The invention relates in its broadest aspect to an ostomy appliance comprising a body side member, an optionally separately exchangeable receiving member or bag secured to the body side ostomy member and further a separate sealing member.

In a second aspect, the invention relates to the use of a mechanical fastening means in the form of snaps, buckles, buttons, rings or mating elements of hook and loop fastening material for securing a separately exchangeable receiving member or bag for receiving secretions from an ostomy to a body side ostomy member.

BRIEF DESCRIPTION OF THE DRAWINGS

The invention is disclosed more in detail with reference to the drawings in which.

DETAILED DESCRIPTION OF THE DRAWINGS

Figure 1:
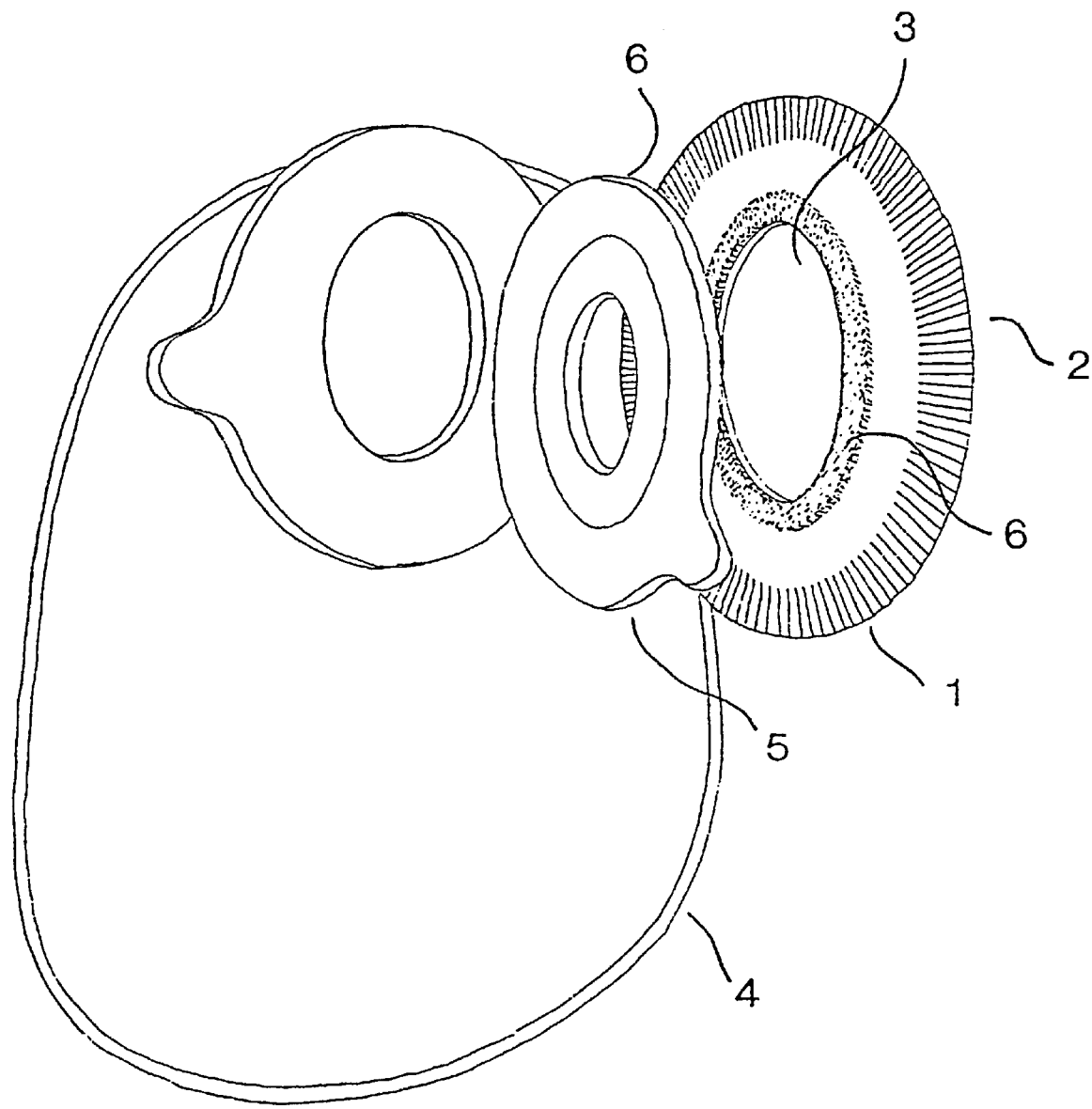
FIG. 1 shows the parts of an ostomy appliance according to the invention.

Reference is made to FIG. 1 which shows an ostomy appliance according to the invention comprising a body side member 1 comprising an adhesive wafer or pad 2 for securing the appliance to the user's skin, said wafer or pad having a hole 3 for receiving a stoma, and a separately exchangeable receiving member or bag 4 which may be secured to the body side ostomy member for receiving secretions from the ostomy said ostomy appliance further comprising a separate sealing member 5 disposed in the hole of the wafer or pad surrounding the stoma wherein the separately exchangeable sealing member is secured releasably to the body side ostomy member by mating elements of hook 6 and loop fastening material.

Figure 2:
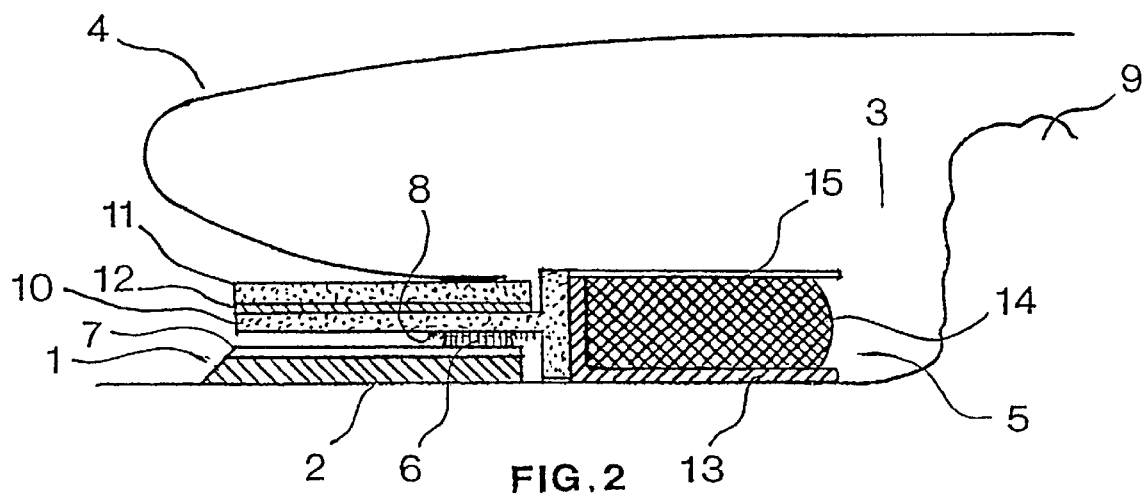
FIG. 2 shows a cross sectional view of a part of an embodiment of the invention.

In the embodiment of FIG. 2, the body side member 1 comprises a body side member 1 comprising an adhesive wafer or pad 2 for securing the appliance to the user's skin, said adhesive being covered by a film 7 conventionally used. Furthermore, the body side member comprises a hook part 6 of a hook and loop fastening material, the loop part 8 being positioned on the separate sealing member 5 disposed in the hole of the wafer or pad surrounding the stoma 9. The loop material is placed on the proximal side of the sealing member on a flange 10, preferably made from a foam material. The receiving member or bag 4 comprises a flange 11 secured to the flange 10 sealing by a layer of an adhesive 12. This adhesive may be any adhesive being detachable from the two flanges in order to allow for an exchange of only the receiving member or bag leaving the body side member and the separate sealing member on the abdomen of the ostomate. It is desirable that the attachment between the receiving member or bag and the separate sealing member is weaker than the attachment between the separate sealing member and the body side member. In this embodiment a layer 13 of a skin friendly adhesive, preferably a medical grade adhesive is positioned on the proximal side of the mouldable adhesive mass 14 of the separate sealing member. Furthermore, the separate sealing member comprises a mouldable backing 15. The sealing member may be open in that the mouldable adhesive mass 14 may be squeezed out between the layer 13 and the mouldable backing 15 in order to seal against the ostomy. In the alternative, the mouldable adhesive mass may be fully enclosed in a thin, flexible and deformable material (wrapping material) allowing for deformation of the mouldable adhesive mass and a sealing against the ostomy.

The wrapping material is thin, flexible and deformable. The wrapping material is either a water permeable membrane coated with a skinfriendly adhesive on the outer side e.g. product 1527 from 3M. The wrapping material may also be a skinfriendly hydrocolloid-containing barrier adhesive. A variety of such barrier adhesives are known in the art and may be used here, one such formulation being discloses, for example in patent DK 147035 and U.S. Pat. No. 4,551,490. The wrapping material improves the performance of the mouldable ring due to elimination of the risk of dissolution of the deformable core material. This also eliminates the risk that residues from the core material should remain on the skin after removal.

The separate sealing member 5 may be made from a mouldable adhesive in the form of a paste of a skin-friendly adhesive being sufficiently tacky to secure the appliance or skin barrier to the abdomen and a cohesion ensuring safe removal thereof without leaving residues on the skin. The sealing member may be composed of one material or may optionally be composed of two or more layers one of which being a mouldable backing and may optionally be covered with a protecting layer or film.

All adhesive surfaces may be protected by release liners to be removed before application.

The separate sealing member 5 may preferably be a uniform mouldable mass of a hypoallergenic, substantially non-memory putty-like adhesive or it may comprise further constituents such as a protecting film or a mouldable mesh.

The separate sealing member 5 may be substituted together with the receiving member 4 leaving the body side member 1 on the skin. It is contemplated that the sealing member may be substituted independently of the receiving member according to the need of the user.

Figure 3:
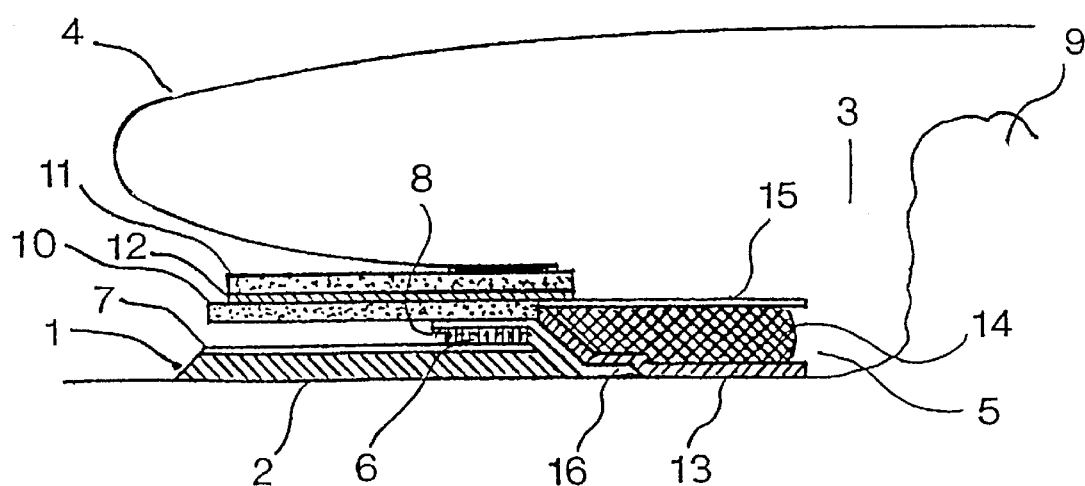
FIG. 3 shows a cross sectional view of a part of another embodiment of the invention.

Now referring to FIG. 3 is described another embodiment of an ostomy appliance of the invention comprising a body side member 1 comprising an adhesive wafer or pad 2 for securing the appliance to the user's skin, said wafer or pad having a hole 3 for receiving a stoma 9, and an optionally separately exchangeable receiving member or bag 4 secured to the body side ostomy member for receiving secretions from the ostomy said ostomy appliance further comprising a separate sealing member 5 disposed in the hole 3 of the wafer or pad surrounding the stoma. In this embodiment, the flange 10 has a greater diameter than the flange 11 in order to facilitate the gripping of only the receiving member or bag leaving the body side member and the separate sealing member on the abdomen of the ostomate. The flange 11 may comprise an ear for an easier identifying the flange when exchanging the receiving member or bag.

In this embodiment, the adhesive wafer 2 and the separate sealing member are bevelled and a layer 16 is present around the rim of the sealing member to avoid undesirable adhesion between the sealing member and of the body side member. The loop part 8 is in this embodiment placed on the layer 16.

The medical grade adhesive secures the sealing member to the peristomal skin. A variety of such barrier adhesives are known in the art and may be used here, one such formulation being disclosed, for example in patent DK 147035 and U.S. Pat. No. 4,551,490. The mouldable adhesive mass is laminated on top of the medical grade adhesive and is used for adapting the sealing member to the stoma by displacing the material inwardly to the stoma by finger pressure. The mouldable adhesive may be composed of a hypoallergenic, soft, easy-deformable, non-memory putty like adhesive material and is preferably a hydrocolloid based adhesive or a hydrogel. The mouldable backing, e.g. Parafilm® or a polymer solution which is sprayed on the surface, protects the surface of the mouldable mass against dissolution by secret from the stoma and prevent a tacky surface on the side facing the bag.

The medical grade adhesive improves the performance due to elimination of the risk of dissolution of the mouldable adhesive mass. This also eliminated the risk of having residues from the mouldable material remaining on the skin after removal. The best performance is achieved if the medical grade adhesive is extended to cover the edges of the mouldable adhesive in order to protect the edges from erosion and dissolution.

The medical grade adhesive secures the unit to the peristomal skin. The flexible backing, protects the surface of the adhesive against dissolution by secretions from the stoma and prevent a tacky surface on the side facing the bag.

This embodiment offers the following advantages: it is simple/easy to handle, it may be adapted to stoma without use of tools, it gives rise to no or very little residues on skin after removal, it gives rise to no or little erosion of adhesive, and it may easily be adapted to complicated shapes of the stoma.

DETAILED DESCRIPTION OF THE INVENTION

The present invention relates to an ostomy appliance comprising a body side member comprising an adhesive wafer or pad for securing the appliance to the user's skin, said wafer or pad having a hole for receiving a stoma, a stoma sealing member and a separately exchangeable receiving member or bag secured to the body side ostomy member for receiving secretions from the ostomy, wherein the separately exchangeable receiving member is secured releasably to the body side member by a mechanical fastening means, said appliance being characterised in that the ostomy appliance further comprises a separate sealing member disposed in the hole of the wafer or pad surrounding the stoma wherein the separately exchangeable receiving member or bag is secured releasably to the body side ostomy member through the separate sealing member by the mechanical fastening means.

It has surprisingly been found that it is possible to provide an ostomy appliance having a separate sealing member disposed in the hole of the wafer or pad surrounding the stoma offering a convenient and comfortable solution to the above problems and that it is, at the same time, possible to separate the two functions of the sealing around an ostomy and the securing of a separately exchangeable receiving member or bag for receiving secretions from an ostomy to a body side ostomy member.

The mechanical fastening means for securing the separately exchangeable receiving member or bag releasably to the body side ostomy member may e.g. be a zip-like fastener, snaps, buckles, buttons, rings or by mating elements of hook and loop fastening material.

A zip-like fastener may e.g. be of the type known for closing plastic bags, e.g. marketed under the trademark Minigrip®.

The preferred mechanical fastening means for securing the separately exchangeable receiving member or bag releasably to the body side ostomy member is mating elements of hook and loop fastening material. Such mating elements may be obtained under the trade mark Velcro®.

Two different types of adhesives can be used for the sealing member—both being adaptable to the stoma without the use of tools.

1. Mouldable adhesives which can be adapted to the stoma by displacement of the adhesive mass inwardly whereby it forms a protective mass surrounding the stoma.

2. Flexible adhesives which can be adapted to the stoma due to the flexibility and compliance whereby it forms a protective layer on the peristomal skin surrounding the stoma.

The mouldable adhesive used in the different compositions of the sealing member is preferably characterised as being a hypoallergenic, substantially non memory putty-like adhesive. It may be e.g. be a homogeneous mixture of a pressure sensitive adhesive component, mineral oil, and hydrocolloid gums or cohesive strengthening agents as the mass disclosed in U.S. Pat. No. 4,204,540. The mass may also be a composition including one or more hydrocolloids, a film former which is a butyl ester of polycarboxylic resin formed from vinyl methyl ether and maleic anhydride, a plasticizer, a thickening agent and an alcohol solvent as disclosed in EP patent No. 0 048 556. A further paste is disclosed in U.S. Pat. No. 5,369,130. This composition comprises a liquid rubber component and a filler component. The rubber component is a diene-type liquid rubber, preferably butadiene- or isoprene-type. The filler component is selected from the groups consisting of inorganic filters, natural polymers, semisynthetic water-soluble polymers and synthetic water-soluble polymers. A further composition of a skin protective gel containing polyvinyl methylether or monoisopropyl ester of polyvinylmethylether maleic acid is disclosed in U.S. Pat. No. 3,876,771. The composition is a made up of a filmforming protective colloidal material in combination with a solvent and a gelling agent. Isopropanol is the solvent, monoisopropyl ester of polyvinyl methylether/maleic acid is a film former and polyvinylpyrrolidone, polyvinyl methylether, polyacrylic acid and hydroxypropyl cellulose are the gelling agents. A hydrophilic elastomeric pressure sensitive material is disclosed in U.S. Pat. No. 4,750,482. This composition is a water-insoluble, hydrophilic, pressure-sensitive adhesive including at least one irradiation cross-linked synthetic organic polymer (predominantly of derived from vinylpyrrolidone) and an adhesive plasticizer (polyethylene glycol).

The composition disclosed in EP 0 048 556 B1 suffers from the drawback that it comprises a considerable amount (25% to 45% by weight) of alcohol, ethanol and isopropanol being preferred. When using such a paste, there it is to be observed that only a limited time for forming the paste after the application as the paste cures when exposed to air. Furthermore, the amount of alcohol trapped in the paste must be minimised in order to avoid less attractive physical properties due to an adverse effect on the properties of the adhesive of an ostomy appliance which is placed upon the paste. Still further, the considerable amount of alcohol may irritate the skin and such a composition is not advisable to use on skin which has been sensibilised.

The pastes disclosed in U.S. Pat. No. 4,204,540 suffers from the drawback that the shapeability is very dependent on the content of mineral oil. If an insufficient amount of mineral oil is added the composition will be too tough to shape and if too much mineral oil is added the composition becomes sticky and difficult to handle. Generally, pastes consisting of polyisobutylene, butyl rubber and mineral oil may be very hard, if the content of butyl rubber is high and hence, the paste will be difficult to shape, or it will be very soft and liquid if the content of butyl rubber is low and the content of mineral oil is high.

The mass used according to the invention is preferably in the form of a mouldable mass of a hypo-allergenic, substantially non-memory putty-like adhesive. In accordance with a preferred embodiment of the invention, the sealing member is made from a mouldable mass of a hypoallergenic, substantially non-memory putty-like adhesive comprising a) a blockcopolymer having a major content of di-block copolymer,
b) a tackifying liquid constituent, and
c) a waxy constituent.

The sealing member may according to the invention be in the form of a paste or in the form of a mouldable ring comprising a hypoallergenic, substantially non-memory putty-like adhesive. In one embodiment of the invention, the sealing member is in the form of a mouldable ring having a slot for facilitating adaptation to stomas having a small diameter.

In a preferred embodiment the sealing member has a flange stretching from the outer rim thereof. Such a flange provides an extra security against leaks and excludes direct contact between the secretions and the coupling part of the ostomy device. Thus, a pollution or contamination of parts of the body side member during service or exchange of receiving member or bag is avoided. Avoidance of pollution or contamination of the body side member is of great importance when extending the weartime of the body side member as remains of the secretion on the body side member which may cause odour are avoided.

Additionally, this embodiment renders it possible to separate the two functions of the sealing around an ostomy and the securing of a separately exchangeable receiving member or bag for receiving secretions from an ostomy to a body side ostomy member in that it is not mandatory that the securing of the separately exchangeable receiving member to the body side ostomy member impervious to liquid.

In a preferred embodiment of the invention, the mechanical fastening means are placed between the separate sealing member disposed in the hole of the wafer or pad surrounding the stoma and the body side member.

This embodiment renders it simple to discriminate between the securing of the separately exchangeable receiving member or bag for receiving secretions from an ostomy and of the separate sealing member disposed in the hole of the wafer or pad surrounding the stoma. Thus, it is simple to decide whether to exchange only the receiving member or bag or to exchange the receiving member or bag and the separate sealing member disposed in the hole of the wafer or pad surrounding the stoma.

In another aspect, the invention relates to the use a mechanical fastening means in the form of snaps, buckles, buttons, rings or mating elements of hook and loop fastening material for securing a separately exchangeable receiving member or bag for receiving secretions from an ostomy to a body side ostomy member of an ostomy appliance comprising a body side member comprising an adhesive wafer or pad for securing the appliance to the user's skin, said wafer or pad having a hole for receiving a stoma, a stoma sealing member and a separately exchangeable receiving member or bag secured to the body side ostomy member for receiving secretions from the ostomy, wherein the separately exchangeable receiving member is secured releasably to the body side member by a mechanical fastening means and wherein the ostomy appliance further comprises a separate sealing member disposed in the hole of the wafer or pad surrounding the stoma wherein the separately exchangeable receiving member or bag is secured releasably to the body side ostomy member through the separate sealing member by the mechanical fastening means.

MATERIALS AND METHODS

Kraton® G1726 from Shell; Styrene-ethylenebutylene-styrene copolymer (SEBS) having a molecular weight of 45,000 as determined by GPC and a content of diblock copolymer of 70%.

Kraton® D1118 from Shell; Styrene-butadiene-styrene copolymer (SBS) having a molecular weight of 103,000 (GPC) and a content of diblock copolymer of 80%.

Vector® 4114 from Exxon; Styrene-isoprene-styrene copolymer (SIS) having a molecular weight of 130,000 and a content of diblock copolymer of 40%

Vistanex® LM-MH from Exxon; polyisobutylene (PIB) having a molecular weight of 90,000 (GPC).

Wax Total 40/60 from TOTAL

Petroleum jelly: Vaselinum Aibum from Witco

Polybutene oil: Hyvis® 10 from BP having a molecular weight of 1,500.

Polybutene: Hyvis® 2000 from BP having a molecular weight $M_w$ of 30,000

Liquid paraffin: PL 500 from Parafluid Mineral Oel

Tackifier resin: Regalite® R91 resin from Hercules or Arkon® P-90 resin from Arakawa Sodium carboxymethylcellulose: Akucell® AF2881 from Akzo or Blanose® 9H4XF from Hercules Corp.

Guar gum: Guar Gum FG 200 from Nordisk Gelatine

Pectin: Pektin LM 12CG Z from Copenhagen Pectin or Pektin USP/100 from Copenhagen Pectin Gelatin: Gelatin P.S.98.240.233 from ED. Gelstlich Sohne AG Zinc Oxide: Zinkoxid Pharma from Hoechst AG A Z mixer Type LKB 025 from Herman-Linden was used.

EXPERIMENTAL PART

EXAMPLE 1

Preparation of a mouldable mass to be used according to the invention.

100 grams of Kraton® G1726 was used and the amounts of other ingredients used correspond to the composition stated in Table 1.

Equal amounts of Kraton® G1726 (SEBS) and of Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and petroleum jelly were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. and mixed for 10 minutes.

The paste is then ready to use and may preferably be packed in metered amounts, e.g. in a blister pack or rod. A rod may be rolled and have a release liner on one or both sides. The product is preferably produced and packed under aseptic conditions.

EXAMPLE 2

Preparation of a mouldable mass to be used according to the invention.

100 grams of Kraton® G1726 was used and the amounts of other ingredients used correspond to the composition stated in Table 1.

Equal amounts of Kraton® G1726 (SEBS) and Vistanex® LM-MH were mixed in a Z Mixer for 20 minutes at 160° C. under a vacuum of 100 mbar. Then, the vacuum was released, the mixing was continued at 160° C. for 10 minutes and the remains of Vistanex® LM-MH, the wax, and Petroleum jelly, polybutene oil or liquid paraffin were admixed and mixed for 10 minutes each. Then, the heating was turned off, and guar gum was added at maximum 90° C. under a vacuum of 100 mbar and mixed for 10 minutes. Finally, pectin, gelatine and zinc oxide were admixed at a temperature of 90° C. mixed for 10 minutes.

The paste is then ready to use and may preferably be packed in metered amounts, e.g. in a blister pack or rod. A rod may be rolled and have a release liner on one or both sides. The product is preferably produced and packed under aseptic conditions.

EXAMPLES 3–5

Preparation of mouldable masses to be used according to the invention.

In the same manner as described in Example 2 above, mouldable masses according to the invention were produced having the compositions stated in the below Table 1:

TABLE 1

Composition of mouldable masses of the invention of Examples 1–5 stated in % by weight

| Component | Example 1 | Example 2 | Example 3 | Example 4 | Example 5 |
|---|---|---|---|---|---|
| SEBS | 5 | 5 | 5 | 10 | 8 |
| PIB | 30 | 15 | 15 | 10 | 18 |
| Microcrystalline wax | 5 | 5 | 5 | 5 | 5 |
| Petroleum jelly | 10 | | | | |
| Polybutene oil | | 25 | | | |
| Liquid paraffin | | | 25 | 25 | 20 |
| CMC | | | 12 | 20 | 15 |
| Guar Gum | 15 | 20 | | | |
| Pectin | 15 | 10 | 10 | 10 | 8 |
| Gelatine | 18 | 17.5 | 27 | 20 | 25 |
| Zinc white | 2 | 2.5 | 1 | | 3 |

EXAMPLE 6

Preparation of a mouldable mass to be used according to the invention.

Equal amounts of Kraton® G1726 (SEBS) and Hyvis® 2000 were mixed in a Z mixer for 30 minutes at 160° C. under a vacuum of 100 mbar and the Hyvis® 2000 was added in four parts to ensure homogeneity during the admixing over a period of 20 minutes. Then, the remains of Hyvis® 2000 was added in four parts at 160° C. over 30 minutes and the vacuum was released. The Hyvis® 10 was added in four parts and mixed for 15 minutes. Wax was added and mixed for 10 minutes. Then, the heating was turned off, and guar gum and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. in a blister pack or rod. A rod may be rolled and have a release liner on one or both sides. The product is preferably produced and packed under aseptic conditions.

EXAMPLES 7–8

Preparation of mouldable masses to be used according to the invention.

In the same manner as described in the Example 2 above, mouldable masses according to the invention were produced having the compositions stated in the below Table 2:

TABLE 2

Composition of mouldable masses of the invention of Examples 6–8 stated in % by weight

| Component | Example 6 | Example 7 | Example 8 |
|---|---|---|---|
| SEBS (Diblock content about 70%) | 5 | | |
| SIS (Diblock content about 40%) | | 5 | |
| SB (Diblock content about 80%) | | | 5 |
| PIB | | 15 | 15 |
| Polybutene ($M_w$ 30.000) | 15 | | |
| Polybutene oil | 25 | 25 | 25 |
| Microcrystalline wax | 5 | 5 | 5 |
| CMC | 10 | 13 | 25 |
| Guar Gum | 15 | | |

TABLE 2-continued

Composition of mouldable masses of the invention of
Examples 6–8 stated in % by weight

| Component | Example 6 | Example 7 | Example 8 |
|---|---|---|---|
| Pectin | 5 | 10 | 8 |
| Gelatine | 18 | 22 | 15 |
| Zinc white | 2 | 5 | 2 |

EXAMPLES 9–10

Preparation of mouldable masses to be used according to the invention.

Equal amounts of Kraton® G1726 (SEBS) and Hyvis® 2000 were mixed in a Z mixer for 30 minutes at 160° C. under a vacuum of 100 mbar and the Hyvis® 2000 was added in four parts to ensure homogeneity during the admixing over a period of 20 minutes. Then, the remains of Hyvis® 2000 was added in four parts at 160° C. over 30 minutes and the vacuum was released. The Hyvis® 10 was added in four parts and mixed for 15 minutes. Resin and wax was added and mixed for 10 minutes each. Then, the heating was turned off, and CMC were added at maximum 90° C. under a vacuum of 100 mbar and mixed for 10 minutes. Finally, pectin, gelatine and zinc oxide were admixed at a temperature of 90° C. and mixed for 10 minutes.

The paste was ready to use and may preferably be packed in metered amounts, e.g. In a blister pack or rod. A rod may be rolled and have a release liner on one or both sides. The product is preferably produced and packed under aseptic conditions.

TABLE 3

Composition of mouldable masses of the invention of
Examples 9–10 stated in % by weight:

| Component | Example 9 | Example 10 |
|---|---|---|
| SEBS (Diblock content about 70%) | 5 | 5 |
| Polybutene ($M_w$ 39,000) | 10 | 5 |
| Polybutene oil | 25 | 25 |
| Resin | 5 | 10 |
| Microcrystalline wax | 5 | 5 |
| CMC | 15 | 15 |

TABLE 3-continued

Composition of mouldable masses of the invention of
Examples 9–10 stated in % by weight:

| Component | Example 9 | Example 10 |
|---|---|---|
| Pectin | 10 | 10 |
| Gelatine | 24 | 24 |
| Zinc white | 1 | 1 |

What is claimed is:

1. An ostomy appliance comprising a body side member (1) comprising an adhesive wafer or pad (2) for securing the appliance to a user's skin, said wafer or pad having a hole (3) for receiving a stoma, a stoma sealing member and a separately exchangeable receiving member or bag (4) secured to the body side member for receiving secretions from the ostomy, wherein the separately exchangeable receiving member is secured releasably to the body side member by a mechanical fastening means (6), the ostomy appliance further comprising a separate sealing member (5) disposed in the hole of the wafer or pad surrounding the stoma wherein the separately exchangeable receiving member or bag (4) is secured releasably to the body side member (1) through the separate sealing member (5) by the mechanical fastening means (6).

2. An ostomy appliance as claimed in claim 1, wherein separately exchangeable receiving member or bag (4) is secured releasably to the body side ostomy member (1) by zip-like fastener, snaps, buckles, buttons, rings or by mating elements of hook and loop fastening material.

3. An ostomy appliance as claimed in claim 2, wherein separately exchangeable receiving member or bag (4) is secured by mating elements of hook and loop fastening material (6).

4. An ostomy appliance as claimed in claim 1, wherein the sealing member (5) is in the form of a mouldable mass or ring of a hypo-allergenic, substantially non-memory putty-like adhesive.

5. An ostomy appliance as claimed in claim 1, wherein the sealing member (5) has a flange extending from the outer rim thereof.

6. An ostomy appliance as claimed in claim 1, wherein the mechanical fastening means (6) are placed between the separate sealing member (5) disposed in the hole (3) of the wafer or pad (2) surrounding the stoma and the body side member (1).

\* \* \* \* \*